United States Patent
McNair et al.

(10) Patent No.: US 10,098,582 B1
(45) Date of Patent: Oct. 16, 2018

(54) CHARACTERIZING SLEEP ARCHITECTURE

(71) Applicant: Cerner Innovation, Inc., Kansas City, KS (US)

(72) Inventors: Douglas S. McNair, Leawood, KS (US); Kanakasabha Kailasam, Olathe, KS (US); William Stadler, Kansas City, MO (US)

(73) Assignee: Cerner Innovations, Inc., Kansas City, KS (US)

( * ) Notice: Subject to any disclaimer, the term of this patent is extended or adjusted under 35 U.S.C. 154(b) by 1137 days.

(21) Appl. No.: 14/279,750

(22) Filed: May 16, 2014

Related U.S. Application Data

(60) Provisional application No. 61/824,104, filed on May 16, 2013.

(51) Int. Cl.
*A61B 5/00* (2006.01)
*A61B 5/0476* (2006.01)
*A61B 5/04* (2006.01)

(52) U.S. Cl.
CPC ........ *A61B 5/4812* (2013.01); *A61B 5/04012* (2013.01); *A61B 5/0476* (2013.01); *A61B 5/7264* (2013.01)

(58) Field of Classification Search
None
See application file for complete search history.

(56) References Cited

U.S. PATENT DOCUMENTS

2002/0095099 A1* 7/2002 Quyen ................. A61B 5/0476
600/544
2004/0122335 A1* 6/2004 Sackellares ........ A61B 5/04008
600/544
2007/0149952 A1* 6/2007 Bland .................. G06F 19/345
604/890.1

OTHER PUBLICATIONS

Roschke et al. Nonlinear analysis of sleep eeg in depression: calculation of the largest lyapunov exponent. Eur Arch Psychiatry Clin Neurosci (1995) 245:27-35.*

(Continued)

*Primary Examiner* — Etsub Berhanu
(74) *Attorney, Agent, or Firm* — Shook, Hardy and Bacon, L.L.P.

(57) ABSTRACT

Systems and methods are provided for quantitatively and objectively characterizing sleep architecture in normal individuals and persons with various health conditions. Embodiments of the invention facilitate characterizing temporal-pattern information of an individual's sleep, such as measured by electroencephalography (EEG), for identifying persons with abnormalities in the temporal-pattern information, sequences or durations of their stages of sleeping ("sleep architecture"), for facilitating selecting appropriate therapy or treatment, and for monitoring the effectiveness of such therapy or treatment. In one aspect, a set of time series are formed by electronically representing and storing information pertaining to brain activity, such as EEG hypnogram or sleep information, over a multi-night span. Information for the timeseries is analyzed, using one or more models, such as nonlinear, self-excited threshold autoregressive (SETAR) or neural network models, for determining a measure of chaotic properties of the timeseries. The largest Lyapunov exponent (LLE) is determined for the time series. Statistical departures of a particular patient's LLE values from one or more reference ranges are determined.

15 Claims, 17 Drawing Sheets

(56) References Cited

OTHER PUBLICATIONS

Roschke et al. Nonlinear analysis of sleep EEG data in schizophrenia: calculation of the principal Lyapunov exponent. Psychiatry Research 56 (1995) 257-269.*
Fell et al. Deterministic chaos and the first positive Lyapunov exponent: a nonlinear analysis of the human electroencephalogram during sleep. Biological Cybernetics 69, 139-146 (1993).*
Stam. Nonlinear dynamical analysis of EEG and MEG: Review of an emerging field. Clinical Neurophysiology 116 (2005) 2266-2301.*

* cited by examiner

| DATE | thresh | % state.2 | LLE | ZQ |
|---|---|---|---|---|
| 6-JAN-12 | 2.9 | 45.7% | 4.6E-02 | 85 |
| 7-JAN-12 | 2.9 | 45.8% | 4.9E-02 | 64 |
| 8-JAN-12 | 2.9 | 37.3% | 6.6E-02 | 96 |
| 9-JAN-12 | 2.9 | 36.9% | 6.7E-02 | 82 |
| 10-JAN-12 | 2.9 | 34.9% | 6.3E-02 | 89 |
| 11-JAN-12 | 2.9 | 38.3% | 6.0E-02 | 110 |
| 12-JAN-12 | 2.9 | 43.7% | 4.1E-02 | 78 |
| 13-JAN-12 | 2.9 | 35.8% | 5.3E-02 | 81 |
| 14-JAN-12 | 2.9 | 31.0% | 5.4E-02 | 86 |
| 15-JAN-12 | 2.9 | 48.5% | 5.3E-02 | 60 |
| 16-JAN-12 | 2.9 | 39.1% | 4.6E-02 | 76 |
| 17-JAN-12 | 2.9 | 36.0% | 5.9E-02 | 93 |
| 18-JAN-12 | 2.9 | 47.8% | 4.8E-02 | 63 |
| 20-JAN-12 | 2.9 | 34.4% | -1.4E-01 | 81 |
| 21-JAN-12 | 2.9 | 30.7% | -8.7E-02 | 24 |
| 22-JAN-12 | 2.9 | 28.0% | 5.1E-02 | 60 |
| 23-JAN-12 | 2.9 | 28.0% | 6.8E-02 | 102 |
| 24-JAN-12 | 2.9 | 40.7% | 4.7E-02 | 56 |
| 25-JAN-12 | 2.9 | 30.0% | 3.9E-02 | 48 |
| 26-JAN-12 | 2.9 | 41.1% | 5.0E-02 | 99 |
| 27-JAN-12 | 2.9 | 41.2% | 2.8E-02 | 76 |
| 28-JAN-12 | 2.9 | 33.5% | 6.2E-02 | 102 |
| 29-JAN-12 | 2.9 | 39.6% | 4.9E-02 | 71 |
| 30-JAN-12 | 2.9 | 54.7% | 4.7E-02 | 42 |
| 31-JAN-12 | 2.9 | 36.2% | 6.5E-02 | 67 |
| 1-FEB-12 | 2.9 | 36.2% | 5.7E-02 | 109 |
| 2-FEB-12 | 2.9 | 37.0% | 6.3E-02 | 87 |
| 3-FEB-12 | 2.9 | 47.4% | 3.9E-02 | 55 |
| 4-FEB-12 | 2.9 | 38.2% | 5.4E-02 | 104 |
| 5-FEB-12 | 2.9 | 35.4% | 4.3E-02 | 65 |
| 6-FEB-12 | 2.9 | 37.1% | 3.9E-02 | 81 |
| 7-FEB-12 | 2.9 | 37.2% | 5.2E-02 | 88 |
| 8-FEB-12 | 2.9 | 42.1% | 5.2E-02 | 105 |
| 9-FEB-12 | 2.9 | 39.3% | 4.0E-02 | 66 |
| 10-FEB-12 | 2.9 | 40.0% | 2.8E-02 | 67 |
| 11-FEB-12 | 2.9 | 39.4% | 5.6E-02 | 80 |
| 12-FEB-12 | 2.9 | 55.4% | 6.1E-02 | 67 |
| 13-FEB-12 | 2.9 | 36.6% | 6.3E-02 | 121 |
| 14-FEB-12 | 2.9 | 40.5% | 5.5E-02 | 92 |
| 15-FEB-12 | 2.9 | 39.1% | 5.4E-02 | 91 |
| 16-FEB-12 | 2.9 | 27.4% | 4.4E-02 | 65 |
| 18-FEB-12 | 2.9 | 35.7% | 5.5E-02 | 82 |
| 19-FEB-12 | 2.9 | 36.1% | 4.7E-02 | 89 |
| 20-FEB-12 | 2.9 | 34.2% | 3.6E-02 | 60 |
| | | | 5.7E-02 | |
| | min | 27.4% | -1.4E-01 | |
| | max | 55.4% | 6.8E-02 | |
| | median | 37.3% | 5.2E-02 | |

*FIG. 3A*

| DATE | thresh | % state.2 | LLE | ZQ |
|---|---|---|---|---|
| 11-JUL-12 | 2.9 | 26.8% | 1.9E-02 | 75 |
| 12-JUL-12 | 2.9 | 29.4% | 5.3E-02 | 94 |
| 13-JUL-12 | 2.9 | 33.0% | 3.4E-02 | 80 |
| 14-JUL-12 | 2.9 | 40.8% | 4.1E-02 | 83 |
| 15-JUL-12 | 2.9 | 39.0% | 2.4E-02 | 86 |
| 17-JUL-12 | 2.9 | 34.9% | 4.8E-02 | 73 |
| 18-JUL-12 | 2.9 | 26.4% | 3.2E-02 | 25 |
| 19-JUL-12 | 2.9 | 40.1% | 4.2E-02 | 80 |
| 21-JUL-12 | 2.9 | 32.9% | 3.3E-02 | 69 |
| 22-JUL-12 | 2.9 | 37.3% | 3.7E-02 | 83 |
| 23-JUL-12 | 2.9 | 31.3% | 3.5E-02 | 79 |
| 24-JUL-12 | 2.9 | 31.2% | 5.2E-02 | 99 |
| 25-JUL-12 | 2.9 | 30.3% | 4.2E-02 | 82 |
| 26-JUL-12 | 2.9 | 23.7% | 2.4E-02 | 66 |
| 27-JUL-12 | 2.9 | 38.8% | 5.3E-02 | 68 |
| 28-JUL-12 | 2.9 | 35.4% | 2.9E-02 | 87 |
| 29-JUL-12 | 2.9 | 43.5% | 4.4E-02 | 88 |
| 30-JUL-12 | 2.9 | 43.2% | 5.4E-02 | 89 |
| 31-JUL-12 | 2.9 | 36.7% | 6.1E-02 | 85 |
| 1-AUG-12 | 2.9 | 37.2% | 5.0E-02 | 88 |
| 2-AUG-12 | 2.9 | 35.4% | 4.1E-02 | 81 |
| 3-AUG-12 | 2.9 | 36.4% | 3.9E-02 | 86 |
| 4-AUG-12 | 2.9 | 37.5% | 3.1E-02 | 71 |
| 6-AUG-12 | 2.9 | 31.9% | 5.4E-02 | 89 |
| 7-AUG-12 | 2.9 | 34.8% | 5.0E-02 | 86 |
| 8-AUG-12 | 2.9 | 52.7% | 3.6E-02 | 65 |
| 9-AUG-12 | 2.9 | 32.0% | 5.3E-02 | 89 |
| 10-AUG-12 | 2.9 | 34.5% | 6.3E-02 | 78 |
| 11-AUG-12 | 2.9 | 34.0% | 3.3E-02 | 67 |
| 12-AUG-12 | 2.9 | 48.2% | 7.6E-02 | 79 |
| 14-AUG-12 | 2.9 | 30.4% | 3.9E-02 | 74 |
| 15-AUG-12 | 2.9 | 39.6% | 5.8E-02 | 98 |
| 16-AUG-12 | 2.9 | 31.9% | 4.0E-02 | 71 |
| 18-AUG-12 | 2.9 | 37.1% | 5.5E-02 | 88 |
| 19-AUG-12 | 2.9 | 35.9% | 6.2E-02 | 86 |
| 22-AUG-12 | 2.9 | 33.7% | 6.0E-02 | 73 |
| 23-AUG-12 | 2.9 | 29.3% | 6.2E-02 | 83 |
| 24-AUG-12 | 2.9 | 51.5% | 6.9E-02 | 77 |
| 25-AUG-12 | 2.9 | 38.6% | 5.6E-02 | 79 |
| 27-AUG-12 | 2.9 | 42.4% | 5.0E-02 | 76 |
| 28-AUG-12 | 2.9 | 37.7% | 4.6E-02 | 94 |
| 29-AUG-12 | 2.9 | 34.0% | 5.0E-02 | 79 |
| 31-AUG-12 | 2.9 | 39.1% | 5.2E-02 | 78 |
| 1-SEP-12 | 2.9 | 32.8% | 6.0E-02 | 64 |
| 4-SEP-12 | 2.9 | 33.9% | 4.0E-02 | 83 |
| | | | 4.6E-02 | |
| | min | 23.7% | 1.9E-02 | |
| | max | 52.7% | 7.6E-02 | |
| | median | 35.4% | 4.8E-02 | |
| | avg | 35.9% | 4.6E-02 | |
| | SD | 5.9% | 1.3E-02 | |
| | CV% | 16.5% | 27.3% | |
| | | | Start | End |
| | total len | 36754 | 6 | 30 |

FIG. 3B

| DATE | thresh | % state.2 | LLE | ZQ |
|---|---|---|---|---|
| 12-JUL-12 | 2.9 | 38.8% | 2.1E-02 | 76 |
| 13-JUL-12 | 2.9 | 38.2% | 4.3E-02 | 89 |
| 14-JUL-12 | 2.9 | 40.9% | 5.5E-02 | 89 |
| 15-JUL-12 | 2.9 | 46.3% | 4.5E-02 | 77 |
| 16-JUL-12 | 2.9 | 43.6% | 2.9E-02 | 71 |
| 17-JUL-12 | 2.9 | 39.7% | 3.0E-02 | 68 |
| 19-JUL-12 | 2.9 | 31.4% | 3.2E-02 | 77 |
| 20-JUL-12 | 2.9 | 50.7% | 3.8E-02 | 43 |
| 21-JUL-12 | 2.9 | 61.6% | 6.6E-02 | 40 |
| 22-JUL-12 | 2.9 | 42.5% | 3.6E-02 | 70 |
| 23-JUL-12 | 2.9 | 41.3% | 2.5E-02 | 81 |
| 25-JUL-12 | 2.9 | 32.6% | 4.5E-02 | 73 |
| 26-JUL-12 | 2.9 | 46.7% | 3.7E-02 | 88 |
| 27-JUL-12 | 2.9 | 41.6% | 3.6E-02 | 55 |
| 29-JUL-12 | 2.9 | 37.3% | 5.0E-02 | 78 |
| 31-JUL-12 | 2.9 | 37.6% | 5.1E-02 | 68 |
| 19-JUL-12 | 2.9 | 34.6% | 2.5E-02 | 66 |
| 20-JUL-12 | 2.9 | 29.6% | 3.4E-02 | 79 |
| 22-JUL-12 | 2.9 | 46.9% | 4.2E-02 | 97 |
| 23-JUL-12 | 2.9 | 39.4% | 3.9E-02 | 80 |
| 27-JUL-12 | 2.9 | 39.4% | 4.0E-02 | 79 |
| 28-JUL-12 | 2.9 | 43.8% | 3.1E-02 | 89 |
| 4-SEP-12 | 2.9 | 34.6% | 4.5E-02 | 93 |
| 16-SEP-12 | 2.9 | 40.8% | 4.7E-02 | 105 |
| 17-SEP-12 | 2.9 | 42.1% | 2.9E-02 | 94 |
| 18-SEP-12 | 2.9 | 41.2% | 3.4E-02 | 89 |
| 19-SEP-12 | 2.9 | 28.6% | 3.9E-02 | 69 |
| 21-SEP-12 | 2.9 | 36.1% | 3.7E-02 | 58 |
| 22-SEP-12 | 2.9 | 36.5% | 2.5E-02 | 77 |
| 23-SEP-12 | 2.9 | 23.0% | 1.9E-02 | 68 |
| 24-SEP-12 | 2.9 | 43.3% | 4.8E-02 | 69 |
| 26-SEP-12 | 2.9 | 42.2% | 4.7E-02 | 92 |
| 27-SEP-12 | 2.9 | 44.6% | 3.4E-02 | 95 |
| 28-SEP-12 | 2.9 | 41.2% | 3.4E-02 | 57 |
| 1-OCT-12 | 2.9 | 44.2% | 4.1E-02 | 84 |
| 2-OCT-12 | 2.9 | 36.9% | 3.8E-02 | 87 |
| 3-OCT-12 | 2.9 | 44.5% | 3.7E-02 | 65 |
| | | | 4.0E-02 | |
| | min | 23.0% | 1.9E-02 | |
| | max | 61.6% | 6.6E-02 | |
| | median | 40.9% | 3.7E-02 | |
| | avg | 40.1% | 3.8E-02 | |
| | SD | 6.7% | 9.7E-03 | |
| | CV% | 16.6% | 25.6% | |
| | | | Start | End |
| | total len | 31385 | 6 | 30 |

*FIG. 3C*

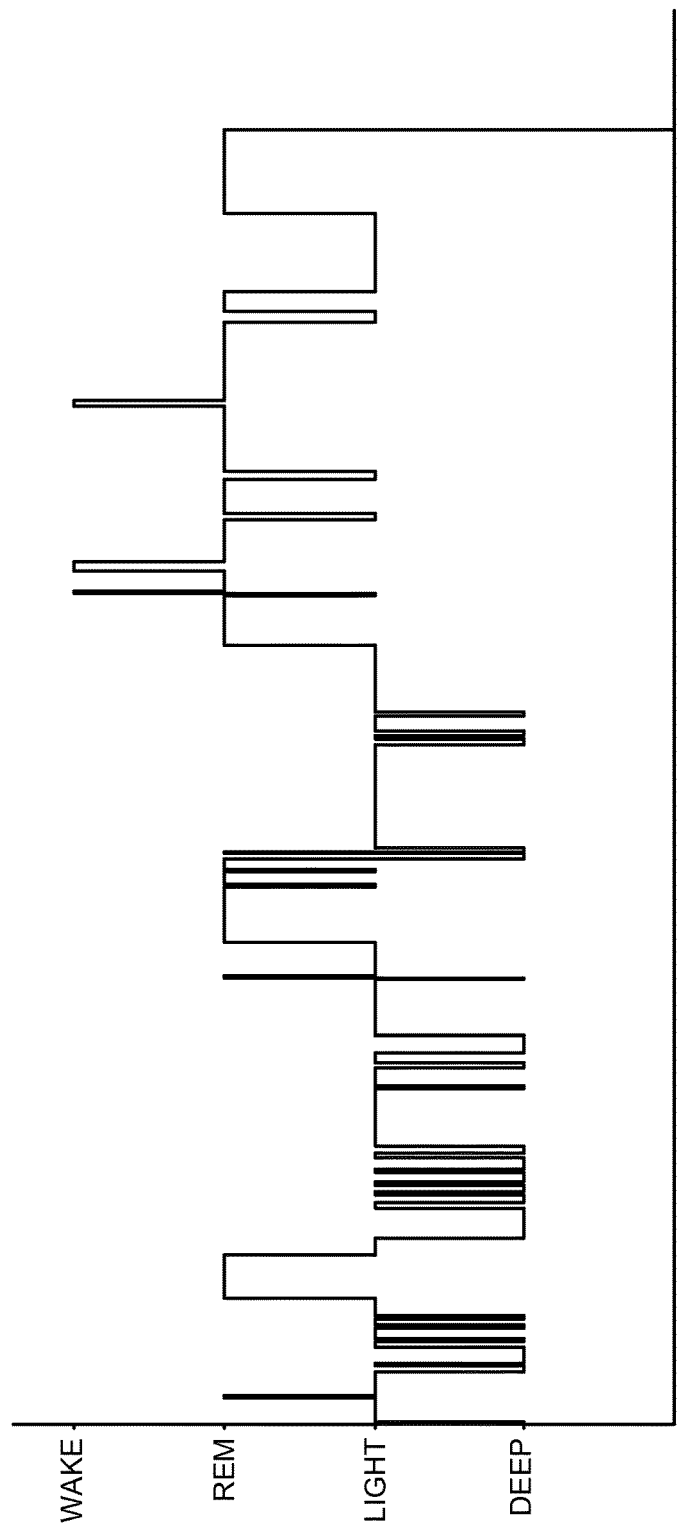

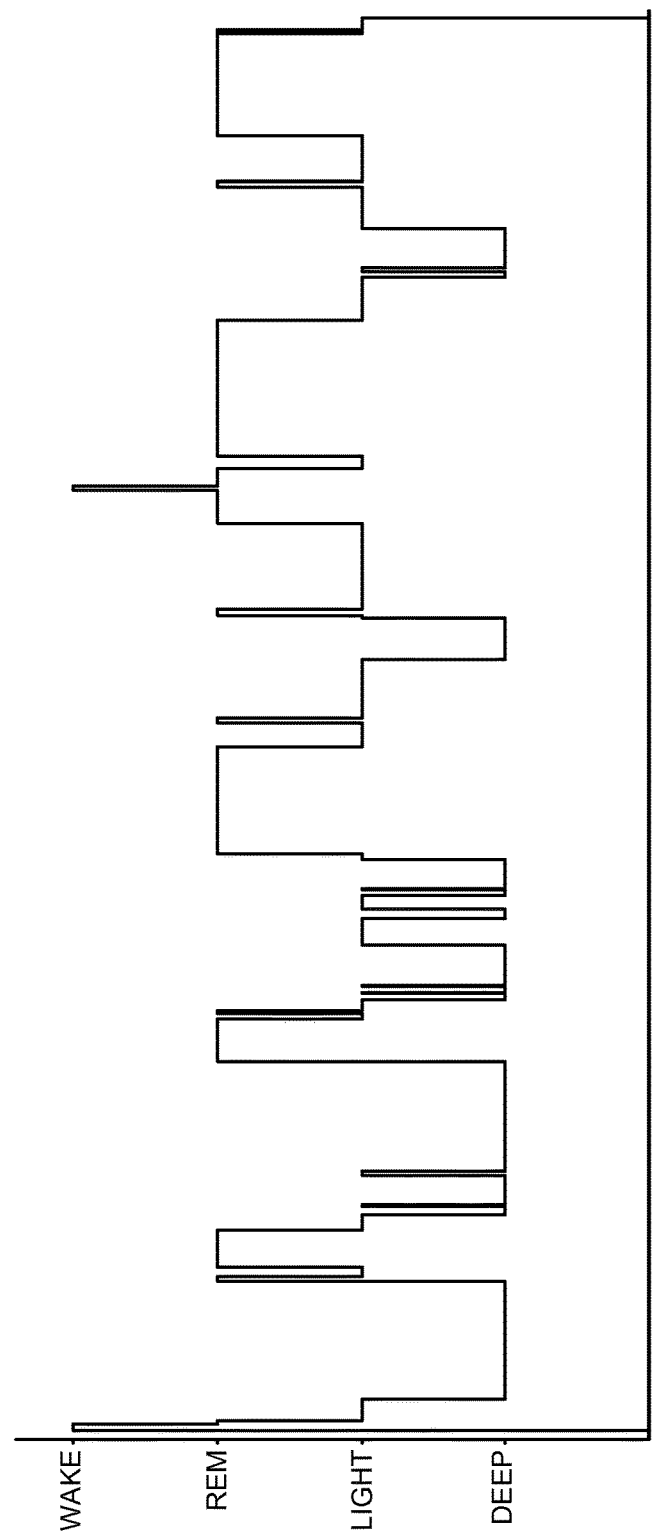

| DATE | thresh | % state.2 | LLE | ZQ |
|---|---|---|---|---|
| 12-Apr-12 | 2.9 | 76.7% | 6.2E-02 | 87 |
| min | | 76.7% | 6.2E-02 | |
| max | | 76.7% | 6.2E-02 | |
| median | | 76.7% | 6.2E-02 | |
| avg | | 76.7% | 6.2E-02 | |
| SD | | #DIV/0! | #DIV/0! | |
| CV% | | #DIV/0! | #DIV/0! | |

FIG. 6A

| | | | | | no nearest neighbors, since total |
|---|---|---|---|---|---|
| unif | 2.9 | 52.2% | 56.7% | N/A | |
| sine | 2.9 | 47.5% | 2.6% | 0.0E+00 | N/A |
| poisson | 2.9 | 76.8% | 33.0% | 3.0E-04 | N/A |
| lorenz.ts | 2.9 | N/A | N/A | 3.0E-01 | N/A |

FIG. 6B.

```
library("tseriesChaos")
library("sm")
library("tsDyn")

# zero-trim left and right tails of detail 30-sec state vector from Zeo
ts <-
c(2,2,1,2,2,2,2,2,2,2,2,2,3,3,2,3,3,3,3,3,3,3,3,3,3,3,3,3,4,4,4,4,4,4,4,4,4,4,4,4,4,4,4,4,4,4,4,
4,4,4,3,3,3,3,3,3,3,2,2,2,2,2,2,2,2,2,2,2,2,2,2,2,2,2,2,2,2,2,2,2,2,2,2,2,2,2,2,2,2,2,2,2,2,2,2,2,
2,2,2,2,2,2,2,2,2,2,2,2,2,2,2,2,2,2,2,2,2,2,2,2,2,2,2,2,2,2,2,2,2,3,3,3,3,3,3,3,3,3,3,3,4,3,4,
4,4,4,4,4,4,4,4,4,4,4,4,4,4,4,4,4,4,4,4,4,4,4,4,4,4,4,4,4,4,4,4,4,4,4,4,4,4,4,4,4,4,4,4,4,4,4,
4,4,4,4,4,4,4,4,4,3,3,3,3,2,2,2,2,3,3,3,3,3,3,3,3,4,4,4,4,4,3,3,3,3,3,4,4,4,4,4,4,4,4,4,4,4,4,
4,4,4,4,4,4,4,4,4,4,4,4,3,3,3,3,3,3,3,3,3,3,3,3,4,4,4,4,4,3,3,3,2,2,2,2,2,2,2,2,2,2,2,2,2,2,
2,2,2,2,2,2,2,2,2,2,2,2,2,3,3,3,3,3,3,3,3,3,3,3,3,3,3,3,3,3,3,3,3,3,3,3,3,3,3,3,3,3,4,4,4,3,3,
4,4,4,4,4,4,4,3,3,3,3,3,3,3,3,4,4,4,4,4,4,4,4,4,4,4,4,4,4,4,4,4,4,4,4,4,4,4,4,4,4,4,4,4,4,4,4,
4,4,4,4,4,4,4,4,4,4,4,4,4,4,4,4,4,4,4,4,4,4,4,4,4,4,4,4,4,4,4,4,4,4,4,4,3,3,3,3)

# transform raw series [states 0 to 4] to 5:missing, 4:wake, 3:REM, 2:light, 1:deep
ds <- 5-ts

# create SETAR nonlinear models;
#         Note1: SETAR occationally gets singular-matrix and Cholesky errors for
# paucidisperse ordinal data
#         Note2: sometimes in very chaotic timeseries the mean absolute percentage error
# (MAPE) exceeds 25% for SETAR
#         Note3: prime-number lag coeffs in low and high regime models give desirable AIC
# values but unstable LLE calc
#                  ds.setar2 <- setar(ds, m=19, d=3, steps=1, ML=c(1,5,7,19), MH=c(1,5,7,19),
# thDelay=1, th=2.9, model="TAR", nthresh=1)
ds.setar2 <- setar(ds, m=2, d=1, steps=10, mL=2, mH=2, thDelay=1, th=2.9, model="TAR",
nthresh=1)
# proportion in state #2 (REM)
ds.setar2$model.specific$RegProp[2]
# threshold cutpoint
ds.setar2$model.specific$coefficients[7]
summary(ds.setar2)
                              .
                              .
                              .

CONTINUES IN FIG. 7B
```

*FIG. 7A*

CONTINUES FROM FIG. 7A

.
.
.

```
# estimate largest Lyapunov exponent (lle) with 200 samples, use lyap_k() and lyap() fns in
# tseriesChaos pkg
# For Kantz algorithm add small amount of observational noise
# ts time series
# m embedding dimension
# d time delay
# s iterations along which follow the neighbours of each point
# t Theiler window
# ref number of points to take into account
# k number of considered neighbours
# eps radius in which to find nearest neighbors

N <- 1000
ds.new <- predict(ds.setar2, n.ahead=N)
ds.new <- ds.new + rnorm(N, sd=sd(ds.new)/50)
sam <- min(500,length(ds.new))
ly <- lyap_k(ds.new, m=2, d=1, t=1, k=2, ref=750, s=sam, eps=sd(ds.new)/2)
plot(ly)

# start Starting time of the initial linear segment of ly
# end Ending time of the linear segment of dsts

lle <- lyap(ly, start=0.1, end=2.3)
lle[2]

lag.plot(predict(ds.setar2, n.ahead=100))

# create neural network nonlinear model; Note4: generally MAPE for NNET is less than 5%,
# except for very short timeseries

ds.nnet <- nnetTs(ds, m=2, size=3)
summary(ds.nnet)
# estimate largest Lyapunov exponent (lle)
N <- 1000
ds.new <- predict(ds.nnet, n.ahead=N)
ds.new <- ds.new + rnorm(N, sd=sd(ds.new)/50)
sam <- min(500,length(ds.new))
ly <- lyap_k(ds.new, m=2, d=1, t=1, k=2, ref=750, s=sam, eps=sd(ds.new)/2)
plot(ly)

lle <- lyap(ly, start=0.1, end=2.3)
lle[2]

# mutual information looks exponential in lags
ds.mutual <- mutual(ds)
```

*FIG. 7B*

CHARACTERIZING SLEEP ARCHITECTURE

CROSS-REFERENCE TO RELATED APPLICATIONS

This application claims the benefit of U.S. Provisional Application No. 61/824,104, titled "NON-LINEAR TIME-SERIES ANALYSIS SYSTEM AND METHOD," filed on May 16, 2013; which is hereby expressly incorporated by reference in its entirety.

INTRODUCTION

Sleep is a complex regulated process with short periods of wakefulness and different sleep stages. Despite some advances in pharmaceutical therapies for sleep disorders; however, disturbed sleep remains widely under-treated. Treatment regimens are selected on a highly subjective basis, and their efficacy goes largely unmeasured. Moreover, conditions such as schizophrenia and other psychoses, unipolar and bipolar depression, Alzheimer's Disease and other dementias, Parkinson's Disease, Post-traumatic Stress Disorder (PTSD), and other mental health conditions are known to have frequent and substantial effects on sleep. Although diminished delta-wave deep sleep and certain other features are detected in a modest percentage of patients, such findings are not consistent or specific.

Despite conjecture about potential REM sleep abnormalities in schizophrenia and other psychiatric disorders, studies comparing patients with healthy control subjects have not revealed consistent abnormalities in the nightly cumulative duration of REM sleep or REM latency or frequency or duration of REM episodes. Slow-wave sleep and non-REM sleep often show some abnormal features, but they are inconsistently manifested such that they are not very practical for purposes of diagnosis or monitoring of treatment efficacy.

The frequency of changes to temporal patterns, sequences, and durations of stages of sleeping ("sleep architecture") and circadian rhythm sleep disturbances increases with age. Although around 40% of older adults complain of poor sleep, true sleep disorders are far less prevalent in healthy older adults and are frequently associated with comorbidities. The sleep disorders observed in Alzheimer's disease (AD) patients are often similar to (but more intense than) those found in non-demented elderly people. Poor sleep results in an increased risk of significant morbidities and even mortality in demented patients and constitutes a major source of stress for caregivers. The prevalence of primary sleep disorders such as rapid eye movement (REM) sleep behavior disorders (RBDs), restless legs syndrome (RLS), periodic limb movements (PLMs) and sleep-disordered breathing increases with age.

Schizophrenia is characterized by disturbed sleep architecture. Some conjecture that schizophrenia constitutes a state that is "trapped" between waking and dreaming. It has been proposed that sleep abnormalities may underlie information processing deficits associated with this disorder. Sleep is also disordered in PTSD and other conditions affecting military personnel.

REM sleep is associated with enhanced activation of limbic and amygdalar networks in the brain and decreased activation in dorsal prefrontal regions, while stage II NREM is associated with greater cortical activation than REM. Not surprisingly, these disparate brain activation patterns tend to be associated with dramatically different phenomenologies with regard to aggressive social interactions. REM and NREM variables may significantly predict daytime mood and social interactions. This is particularly relevant to the effective management of psychiatric conditions that are prone to daytime agitation, self-injury, or violent behavior.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Systems, methods, and computer-readable media are provided for quantitatively and objectively characterizing sleep architecture in normal individuals and in persons with various health conditions, particularly psychiatric conditions, dementia, and individuals who are receiving medications that may alter sleep health. For example, some embodiments of the invention facilitate quantitatively and objectively characterizing temporal-pattern information of an individual's sleep, such as measured by electroencephalography (EEG), for identifying individual persons with abnormalities in the temporal-pattern information, sequences or durations of their stages of sleeping ("sleep architecture"), for facilitating selecting appropriate therapy or treatment, and for monitoring the effectiveness of such therapy or treatment. Some embodiments facilitate evaluating the impact of particular treatments or therapies on a user's sleep, such as side effects resulting from pharmaceutical treatments, therapies, or user-lifestyle changes. Furthermore, in some scenarios, embodiments may facilitate longitudinal, ongoing assessments of a user or patient by engaging the patient to acquire temporal pattern information, such as EEG signals, using inexpensive equipment on a nightly basis in the patient's home.

In one aspect, a set of one or more time series are formed by electronically representing and storing information pertaining to brain activity, such as EEG hypnogram or sleep information, over a multi-night span. Information for a timeseries is analyzed, using one or more timeseries models, such as nonlinear, self-excited threshold autoregressive (SETAR) or neural network models, for determining a measure of chaotic properties of the timeseries. The largest Lyapunov exponent (LLE) is determined for the time series. Statistical departures of a particular patient's LLE values from one or more reference ranges are determined.

BRIEF DESCRIPTION OF THE DRAWINGS

Embodiments are described in detail below with reference to the attached drawing figures, wherein:

FIGS. 3A, 3B, and 3C each provide a table of sleep-related metrics determined for a particular user, in accordance with embodiments of the present invention;

FIGS. 4A, 4B, and 4C each provide a representation of sleep states vs. time for a particular user for a night;

FIGS. 6A and 6B provide a table of sleep-related metrics determined for a particular user, in accordance with embodiments of the present invention;

FIGS. 7A and 7B illustratively provide one example embodiment of a computer program routine for trajectory mining.

DETAILED DESCRIPTION

Figure 1A:
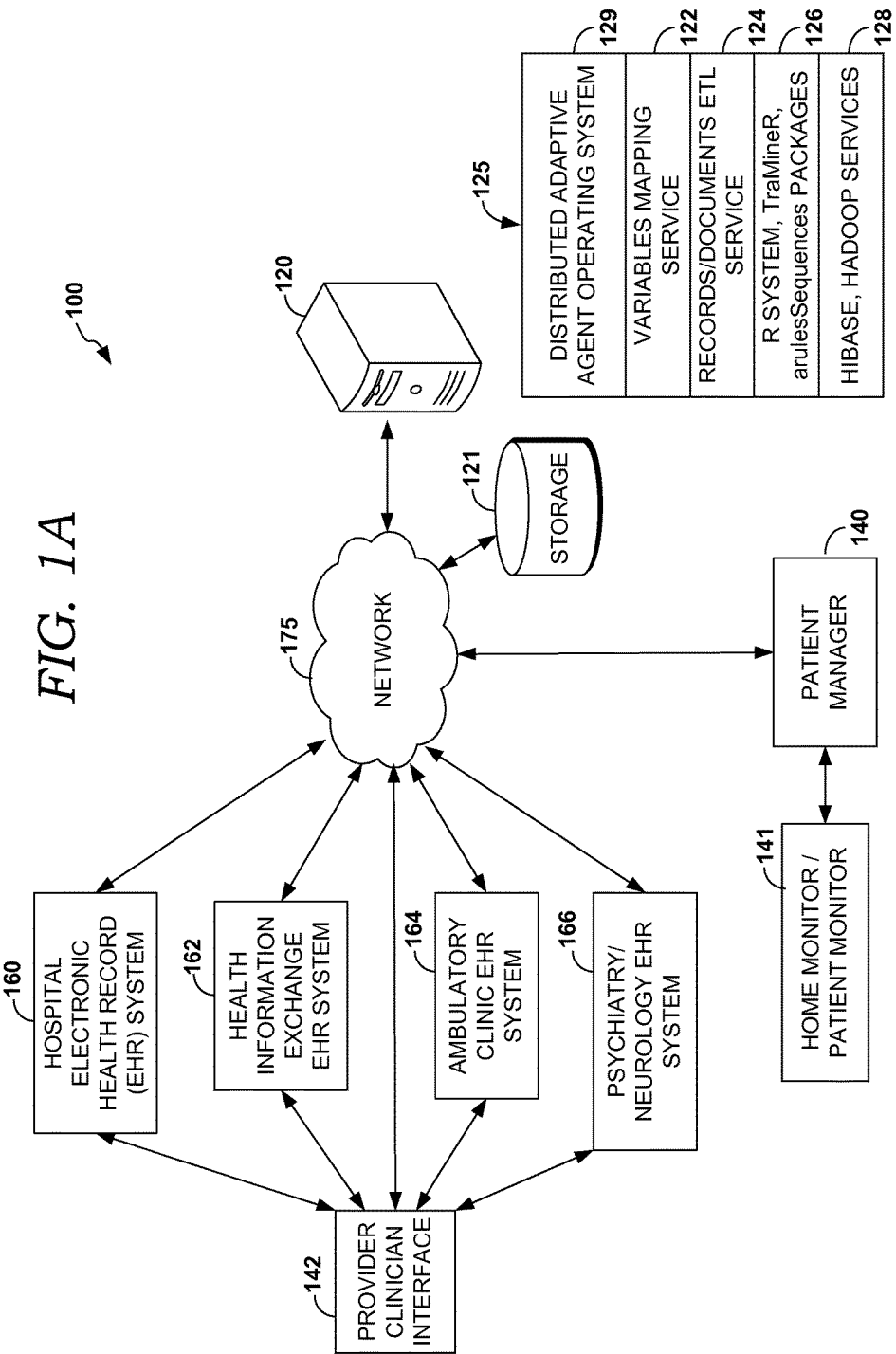
FIGS. 1A, 1B and 1C depict aspects of an exemplary operating environment suitable to implement embodiments of the present invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Embodiments of the invention are directed to methods, computer systems, and computer-readable media for quantitatively and objectively characterizing sleep architecture in normal individuals and in persons with various health conditions such as psychiatric conditions, dementia, or individuals who are receiving therapy, treatment including treatment from medications, or exposure to environmental factors that may alter sleep health. Embodiments may facilitate identifying persons having abnormalities in temporal patterns and sequences and durations of their stages of sleeping ("sleep architecture"), and selecting appropriate treatment or therapy, and monitoring the effectiveness of such treatment or therapy.

Other attempts or efforts at characterizing sleeping conditions are deficient due to: (1) methods utilizing electroencephalography (EEG) and polysomnography (PSG), which focus on (a) "low-level" EEG waveform data and frequency-domain spectral analysis of that and on (b) "summary" data dealing with percentages of time spent in each sleep stage, latency of sleep onset, latency to REM onset, latency to Stage-2 onset, percent waking after sleep onset, number of waking epochs per night, sleep efficiency, and other broad, descriptive features. In particular, both (a) and (b) have only weak statistical correlation with psychiatric conditions, their severity, or their symptomatology during treatment. Additionally, such measures exhibit strong age-dependence among normal individuals, which complicates accurate interpretation, insofar as there are no well-established normative data for these measures' ranges of values in different age groups of persons with psychiatric conditions.

(2) Some efforts rely largely on human interpretation, which is often subjective, inconsistent, and plagued by low sensitivity (many false-negative errors) and low specificity (many false-positive errors). Frequently, humans fail to notice relevant patterns. Often, this is because the patterns involve multiple variables or longitudinal sequences that exhibit high degrees of variability or in other ways elude human detection of signals and statistical associations of signals with clinical states.

(3) Persons with disturbed sleep architecture are poorly able to report on their sleep quality, and virtually none is able to accurately characterize temporal properties of their patterns of sleeping and wakefulness during the night.

(4) Some efforts tend to "medicalize" the process of observation of sleep architecture, such that physicians, nurses, neurophysiologists, somnographers, or other clinical providers have the only active roles in measuring the phenomena of the patient's sleep, and the patient and family members are made to be passive-disempowering them from participating meaningfully in the processes of discovering what is wrong and managing it.

(5) Some efforts are not amenable to periodic or continuous monitoring usage, whereby the patient, their caregivers, and their clinician providers are able to serially assess trends and changes, including either ones that arise with progression of the patient's illness or ones that materialize as responses to the treatment of the illness. As such, there is a high prevalence of ineffectively treated psychiatric conditions in which the medication regimen and the doses of the medicines that comprise the regimen are empirically selected without adequate means to assess the efficacy of the regimen in addressing insomnia or other disturbances of sleep architecture that are associated with the illness.

(6) Alternative efforts that require detailed construction of database retrieval extracts where the extracted cohorts embody homogeneous populations give rise to labor-intensive activities requiring individuals of high levels of expertise. As a result, such systems are too expensive to operate on a comprehensive or sustainable basis.

(7) While conventional EEG and PSG aims to utilize raw and processed biometric signals to ascertain abnormalities in mental health conditions, the signals are only acquired from one or a few nights' studies, and therefore suffer from low sensitivity if abnormalities are not manifested on the particular night or nights studied. Additionally, such studies are expensive to perform and rely on expert polysomnographers and electroencephalographers who are in short supply and generally available only in large metropolitan locations, limiting access that patients have to such services. Furthermore, the studies are conducted in specially-designed sleep labs, such that the unfamiliar environment in the lab may induce sleep patterns that are not representative of patterns that characterize the patient's sleep under ordinary conditions at home. This contributes to a high percentage of false-negative and "data inadequate for evaluation" results.

(8) Some efforts that rely on human interpretation of EEG or PSG studies produce a high rates of false-positive interpretive errors as well.

Accordingly, it is therefore highly valuable and highly desirable to provide embodiments of the methods and systems described herein for quantitatively and objectively characterizing sleep architecture, and which also mitigate the aforementioned limitations.

Nonlinear analyses of sleep data can provide valuable information on sleep characteristics that may be relevant to the functions of sleep, for example analysis of the predictability and nonlinear complexity of sleep EEG time series using measures of nonlinearity, such as symbolic dynamics and the largest Lyapunov exponent (LLE) in schizophrenia. In one analysis, a series of antipsychotic naive patients with first episode of schizophrenia or schizoaffective disorder and age-matched healthy controls were studied during awake period, stage 1/2, slow wave sleep (stage 3/4) and rapid eye movement (REM) sleep. Nonlinearity scores were significantly lower during awake stage in patients compared to controls suggesting that there may be a diminished interplay between various parameters for the genesis of waking EEG. This particular study examines only raw EEG signals and not LLE or other measures in hypnogram time series classified epochs, nor does the study examine multi-night serial EEGs or aggregate statistical properties of multi-night sets of EEGs.

Additionally, other studies have previously evaluated Lyapunov exponents of raw EEG signals during different sleep stages and shown positive Lyapunov exponents during deep sleep, such as obtaining a value of $\lambda=0.4$-$0.8$ for stage II and a value of $\lambda=0.3$-$0.6$ for stage IV. One study reported a greater value of $\lambda=2.1$ for sleep stage II, but concluded that an accurate value is impossible to obtain because of the complexity of the signal, its time varying nature and the sensibility of the results with the election of the parameters for the calculations. Another example, modifying the Wolf algorithm, calculated the Lyapunov exponent of EEG recordings from 15 healthy male subjects in sleep stages I, II, III, IV and REM. They found in all cases positive values, thus stating that EEG signals are neither quasi-periodic waves nor simple noise. These and similar studies address non-linear and stability measurements of raw EEG waveform data. However, none of these studies have reported on non-linear and stability measurements of epochal hypnographic time series data classified as to sleep state or stage during each epoch. Accordingly, embodiments of the invention have determined that the largest Lyapunov exponent in majority of multi-night hypnography time series is significantly positive with an estimated value $\lambda\sim0.02$ to $0.08$ using, in some embodiments, the direct method for estimating the LE of Wolf et al. [1985] and the method of Kantz [Hegger 1999].

Turning now to FIG. 1A there is presented an example operating environment 100 suitable for practicing embodiments of the invention. Example operating environment 100 includes a computerized system for compiling and/or running an embodiment of a sleep architecture characterization decision support recommendation service. With reference to FIG. 1A, one or more electronic health record (EHR) systems, such as hospital EHR system 160, health information exchange EHR system 162, ambulatory clinic EHR system 164, psychiatry/neurology EHR system 166 are communicatively coupled to network 175, which is communicatively coupled to computer system 120. In some embodiments, components of operating environment 100 that are shown as distinct components may be embodied as part of or within other components of environment 100. For example, the one or more EHR systems 160-166 may be implemented in computer system 120. Similarly, a single EHR system may perform functions for two or more of the example EHR systems shown in FIG. 1A.

In embodiments, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) systems 160, 162, 164, and 166 include one or more data stores of health records, which may be stored on storage 121, and may further include one or more computers or servers that facilitate the storing and retrieval of the health records. In some embodiments, one or more EHR systems 160, 162, 164, and 166 may be implemented as a cloud-based platform or may be distributed across multiple physical locations. EHR systems 160, 162, 164, and 166 may further include record systems, which store real-time or near real-time patient (or user) information, such as wearable, bedside, or in-home patient monitors, for example.

Although FIG. 1A depicts multiple example EHR systems, it is contemplated that some embodiments may employ only one EHR system, or alternatively, may rely on user manager 140 and/or monitor 141 for storing and retrieving patient record information such as information acquired from monitor 141.

Example operating environment 100 further includes provider clinician interface 142 communicatively coupled to the one or more EHRs 160, 162, 164, and 166. Although environment 100 depicts a direct communicative coupling between interface 142 and the one or more EHRs 160, 162, 164, and 166, it is contemplated that some embodiments of interface 142 may be communicatively coupled to the EHRs through network 175. Embodiments of interface 142 may take the form of a user interface operated by a software application or set of applications on a client computing device such as a personal computer, laptop, smartphone, or tablet computing device. In one embodiment, the application includes the PowerChart® software, manufactured by Cerner Corporation. In an embodiment, the application is a Web-based application or applet. Provider clinician application facilitates accessing and receiving information from a user or health care provider about a specific patient or set of patients for which sleep architecture characterization is to be performed and facilitates the display of results, recommendations or orders, for example. In some embodiments interface 142 also facilitates receiving orders for the patient from the clinician/user, based on the results. In some embodiments, interface 142 may also be used to display patient sleep-information such as illustratively provided in FIGS. 3-6 and FIG. 8. Additionally, interface 142 may use used for providing diagnostic services, such as evaluating regression models discussed in connection to FIG. 2.

Example operating environment 100 further includes computer system 120, which may take the form of a server, which is communicatively coupled through network 175 to EHR systems 160, 162, 164, and 166, storage 121, and user manager 140.

Embodiments of user manager 140 may take the form of a user interface and application, which may be embodied as a software application operating on one or more mobile computing devices, tablets, smart-phones, front-end terminals in communication with back-end computing systems, laptops or other computing devices. In some embodiments, manager 140 includes a Web-based application or set of applications that is usable to manage user services provided by embodiments of the invention. For example, in some embodiments, manager 140 facilitates processing, interpreting, accessing, storing, retrieving, and communicating information acquired from monitor 141. In some embodiments, manager 140 is used to display user (or patient) sleep-information such as illustratively provided in FIGS. 3-6 and FIG. 8. Similarly, a user (who may be a patient) may access and view records of sleeping-patterns or analyses of previous sleep time intervals using manager 140. Moreover, in some embodiments of manager 140, an interface component may be used to facilitate access by a user to functions or information on monitor 141, such as operational settings or parameters, user identification, user data stored on monitor 141, and diagnostic services or firmware updates for monitor 141, for example.

As shown in example environment 100, manager 140 is communicatively coupled to monitor 141 and to network 175. Embodiments of monitor 141 comprise one or more sensor components operable to acquiring biometric or sleep-related information about a user, such as information associated with a particular physical or mental state or the user, and which may be acquired periodically or as one or more time-series. In some embodiments, monitor 141 comprises a sensor component operable for sensing a user's temporal activity, such as sensing EEG signals derived from the user. In some embodiments, muscle activity, which might be sensed from electromyogram signals, eye movement, which might be sensed from electro-oculogram signals, or other biometric information may be employed.

In some embodiments, one or more sensor components of monitor 141 may comprise a user-wearable sensor component or sensor component integrated into the user's or patient's living environment. Examples of sensor components of monitor 141 include wherein the sensor is positioned on or near the user's head, attached to the user's clothing, worn around the user's head, neck, leg, arm, wrist, ankle, etc., skin-patch sensor, ingestible or sub-dermal sensor, or wherein sensor component(s) are integrated into the user's living environment (including the bed, pillow, or bathroom), sensors operable with or through a smart phone carried by the user, for example.

Embodiments of monitor 141 may store user-derived data locally or communicate data over network 175 to be stored remotely. In some embodiments, manager 140 is wirelessly communicatively coupled to monitor 141. Manager 140 may also be embodied as a software application or app operating on a user's mobile device. In some embodiments, manager 140 and monitor 141 are functional components of the same device, such as a device comprising a sensor and a user interface. In some embodiments, manager 140 is embodied as a base station, which may also include functionality for charging monitor 141 or downloading information from monitor 141.

Figure 1B:
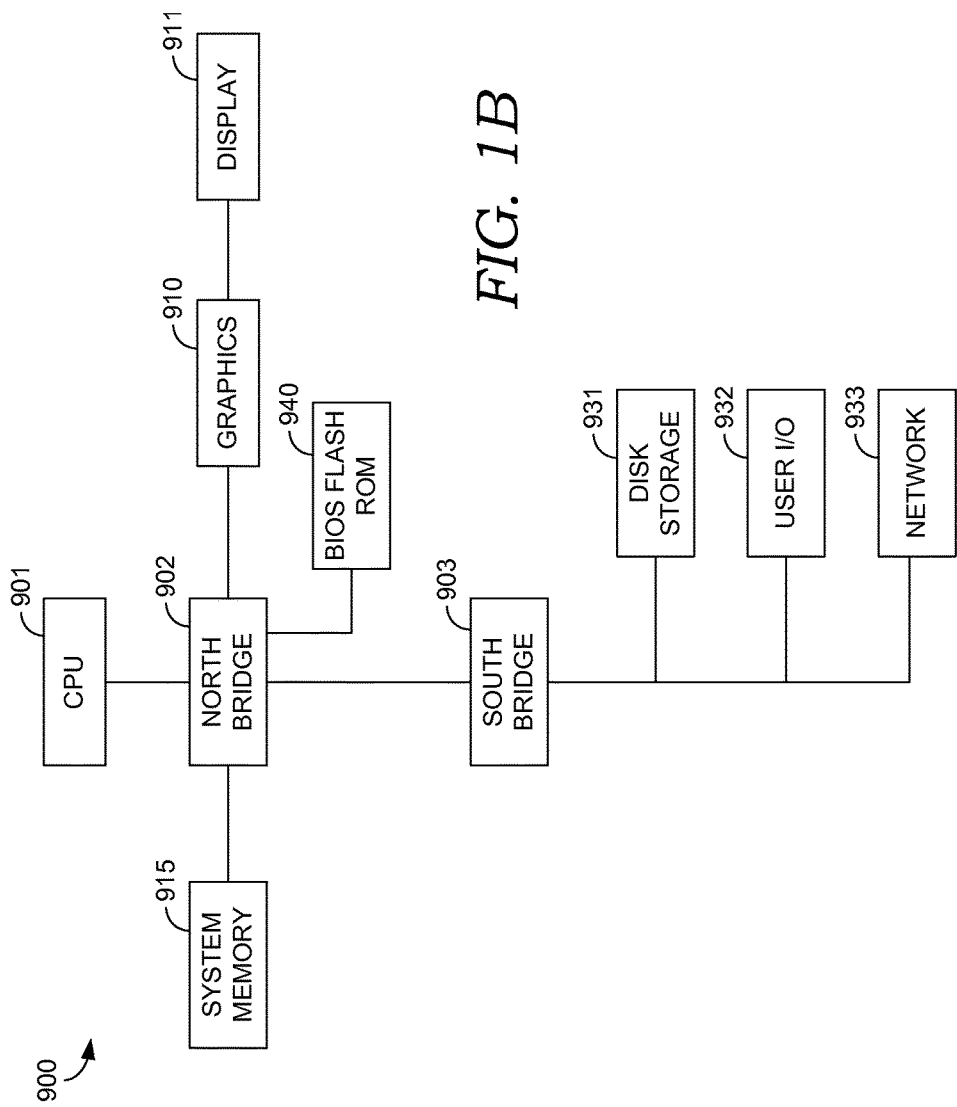
Figure 1C:
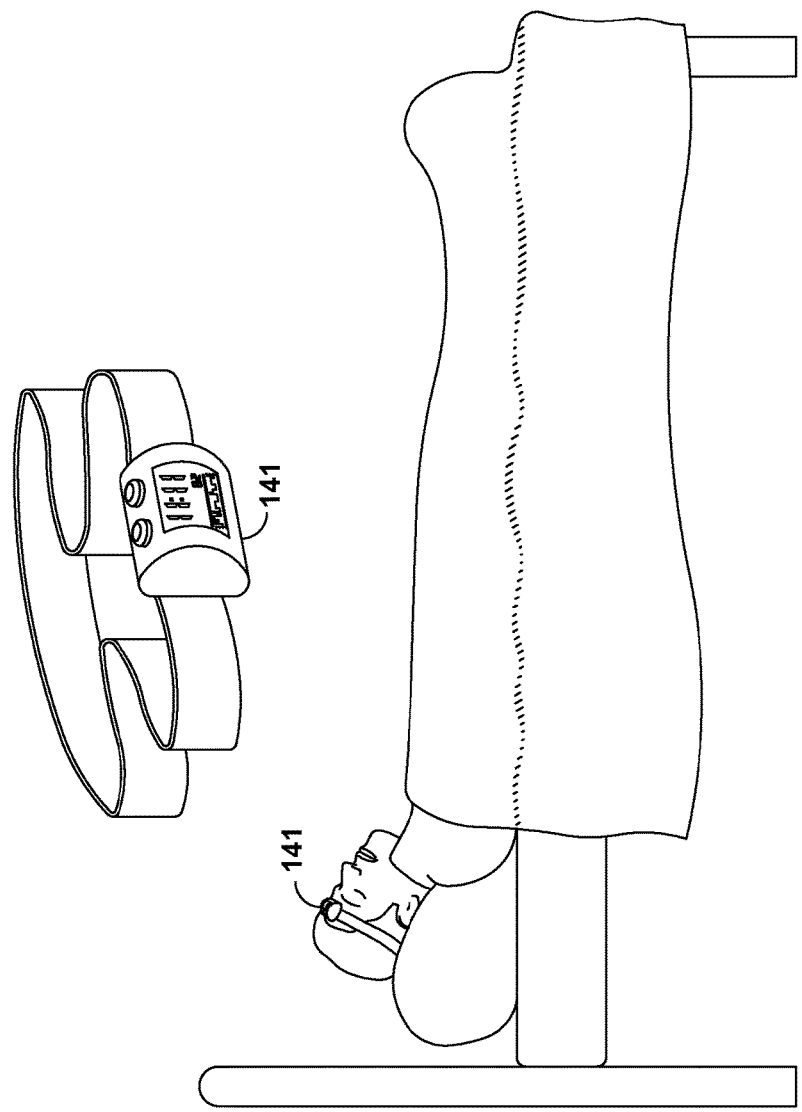

Turning briefly to FIG. 1C, an example embodiment of monitor 141 is shown. In this embodiment, monitor 141 is worn on the user's head and may be worn while the user is sleeping, as shown. Further, in this example embodiment, monitor 141 is attached to a strap to be worn around the user's head thereby positioning monitor 141 to be near the user's head. Additionally, the example embodiment of monitor 141 shown in FIG. 1C includes some functionality of manager 140. For example, this embodiment of monitor 141 includes a user interface with functionality for configuring operational settings, such as on and off or settings for storing and/or communicating sleep-related information acquired from the user information, such as uploading the information to manager 140 or to storage 121, and display functionality for viewing or reviewing sleep-related information acquired from the user. In one embodiment, monitor 141 is embodied as a Zeo™ sleep sensor headband manufactured by Zeo Inc. of Newton, Mass.

With reference to FIG. 1A, some embodiments of monitor 141 include analog-to-digital (A/D) converters for converting analog acquired information into digital information. For example, in one embodiment, user information is acquired at 512 samples per second. Because sleeping-related signals include low frequencies in comparison to other biological signals, an appropriate sampling rate is determined to adequately capture information sufficient to characterize a user's sleep architecture. For example, Delta or Theta cycles have comparatively low frequencies.

In embodiments, monitor 141 includes functionality for processing user-derived information locally or for communicating the information to computer system 120 or manager 140, where it may be processed. In some embodiments, the processing may be carried out or facilitated by one or more software agents, as described below. In some embodiments the processing functionality, which may occur on monitor 141, manager 140 and/or computer system 120 includes signal conditioning, such as removing noise or erroneous information. In some embodiments processing functionality is operable to process user-derived information, such as EEG waveform data, as it is acquired, continuously or periodically such as every 10, 15, or 30, 60 seconds or every few minutes. In some embodiments, the processing includes classifying the user-derived information acquired for a particular time interval into a sleeping category. For example, in some embodiments, monitor 141 samples a user's EEG information and processes (or communicates to manager 141 or computer system 120 for processing) the information approximately every time interval to classify the user's sleep state for that time interval. For example, every 30 second time interval, the user's sleeping state may be determined to be one of stage 1, stage 2, etc., theta, delta, etc., or awake, light sleep, REM sleep, deep sleep, or undetermined. Furthermore, in some embodiments, processing further includes determining a sleep score or sleep number, which qualities the sleep state. In some embodiments, this sleep score is based on the number of time intervals occurring within the sleep categories, for a user, over a night. In embodiments of monitor 141 comprising a Zeo sleep sensor device, described above in connection to FIG. 1C, some models of the Zeo device include functionality for determining a number quantifying the user's sleep based on total sleeping time, and time spent in various sleep states, which is referred to as a ZQ (for Zeo Quotient).

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120. Some embodiments of software stack 125 include a distributed adaptive agent operating system 129, which may be implemented as a platform in the cloud, and which is capable of hosting a number of services such as 122, 124, 126, and 128. Embodiments of services 122, 124, 126, and 128 run as a local or distributed stack in the cloud, on one or more personal computers or servers such as system 120, and/or a computing device running manager 140. In one embodiment, manager 140 operates in conjunction with software stack 125.

In embodiments, variables indexing service 122 and records/documents ETL service 124 provide services that facilitate retrieving frequent item sets, extracting database records, and cleaning the values of variables in records. For example, variables indexing service 122 may perform functions for synonymic discovery, indexing or mapping variables in records, or mapping disparate health systems' ontologies, such as determining that a particular medication frequency of a first record system is the same as another record system. In some embodiments, these services may invoke software services 126. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including tsDyn or similar services for facilitating implementation of non-linear autoregressive time series models, tseriesChaos for nonlinear time series operations, or arulesSequences or similar services for facilitating operations such as K-nearest neighbor distance calculations. Software packages 126 are associated with services 128, which include Apache Hadoop and Hbase framework, or similar frameworks operable for providing a distributed file system, and which in some embodiments facilitate provide access to cloud-based services such as those provided by Cerner Healthe Intent®.

Example operating environment 100 also includes storage 121 or data store 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rule-bases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data stores associated with the one or more EHR systems, such as 161, 162, 164, and 166 and complexity trajectory manager 140. Further, although depicted as a single storage data store, data store 121 may comprise one or more data stores, or may be in the cloud.

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
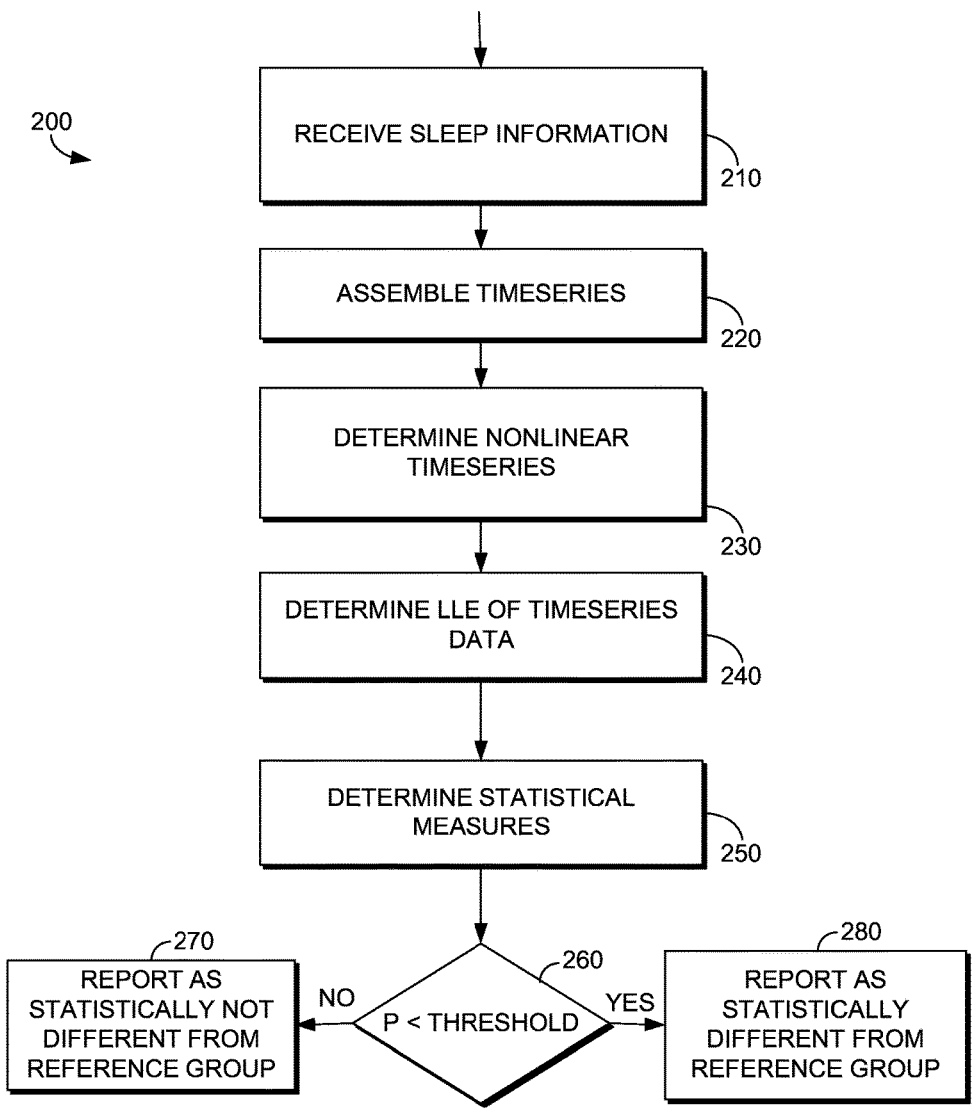
FIG. 2 depicts a flow diagram of a method for characterizing sleep patterns, in accordance with embodiments of the present invention.

Turning now to FIG. 2, a flow diagram is provided for an embodiment of a method for characterizing sleep architecture and detecting abnormal sleep patterns including pattern such as may reflect symptoms and disease processes in mental health conditions (including, but not limited to, dementia, depression, PTSD, Parkinson's Disease, schizophrenia and other psychoses, manic and hypomanic conditions) and for monitoring the efficacy of the management thereof, and referred to generally herein as method 200.

With reference to FIG. 2, when testing for nonlinearity and in particular chaos in timeseries, two quantities may be derived from a timeseries. First, one can estimate the correlation dimension, which measures the fractal nature of a possibly underlying "strange attractor." Secondly, one can estimate the largest Lyapunov exponent (LLE, $\lambda$) which, when found to be positive, measures the sensitive dependence on initial conditions that are characteristic of a chaotic system.

Methods for measuring a degree of order or disorder or to detect the presence of chaos, however, are highly sensitive to noise. In particular, estimation of the correlation dimension is frequently difficult for timeseries. One statistical test for independence, known as the BDS-test, is based on the correlation integral, which can be used as a general specification test. In some embodiments, a more direct test for chaos is asymptotic distribution of a nonparametric neural network estimator of the Lyapunov exponent of a noisy system, since one frequently used definition of chaos is a positive largest Lyapunov exponent.

Some embodiments of the invention have determined that the largest Lyapunov exponent in majority of multi-night hypnography time series is significantly positive with an estimated value $\lambda \sim 0.02$ to $0.08$ using the direct method for estimating the Lyapunov exponent of Wolf et al. and the method of Kantz.

The largest Lyapunov exponent (LLE, $\lambda$) to characterize the behavior and stationarity (or lack thereof) of a system: $\lambda < 0$ means that the trajectory is stable and moves towards a fixed point; $\lambda = 0$ holds for periodic systems; and $\lambda > 0$ is an indication for chaotic or stochastic systems. A positive Lyapunov exponent implies chaos, but one can practically compute finite-time approximations to the exponent. There is a distribution of finite-time exponents over samples of the orbit, and thus even if the true system has a zero or negative largest exponent, it is possible that any particular finite-time sample will register a significantly positive Lyapunov exponent statistic. A statistical test of a collection of several dozen finite-time samples accounts for this source of fluctuations.

Embodiments of the invention have shown that normal, healthy individuals have small positive median LLE (normal range 0.02 to 0.08) in samples of 40 or more nights of sleep. Less than 5% of samples from normal, healthy individuals have LLE $\lambda < 0$. By contrast, multi-night samples from individuals with depression and other psychiatric conditions show median LLE that may be either more negative (indicating entrainment into stationary patterns) or more positive (indicating nonstationary patterns that are more chaotic than those of normal, healthy individuals). A large proportion of samples from persons who have an untreated psychiatric condition that affects sleep architecture show LLE $\lambda$ outside the normal range. The degree to which LLE is normalized for an individual undergoing treatment may provide an indication that such conditions are being effectively treated.

Continuing with FIG. 2, at a step 210 of method 200 receive sleep information for a target such as a user (or patient) or group of users (or patients) and for one or more relevant reference populations. In some embodiments, step 210 comprises receiving multiple nights' hypnographic timeseries information for target user(s), such as provided by monitor 141 or previously acquired sleep information in user data or patient records from an EHR system and receiving time series statistics for hypnogram sets from relevant reference populations. In some embodiments the information comprises timeseries including characterizations of one or more individual's sleeping states over recurring time interval (such as every 30 seconds) over the course of a night, for multiple nights.

Figure 4B:
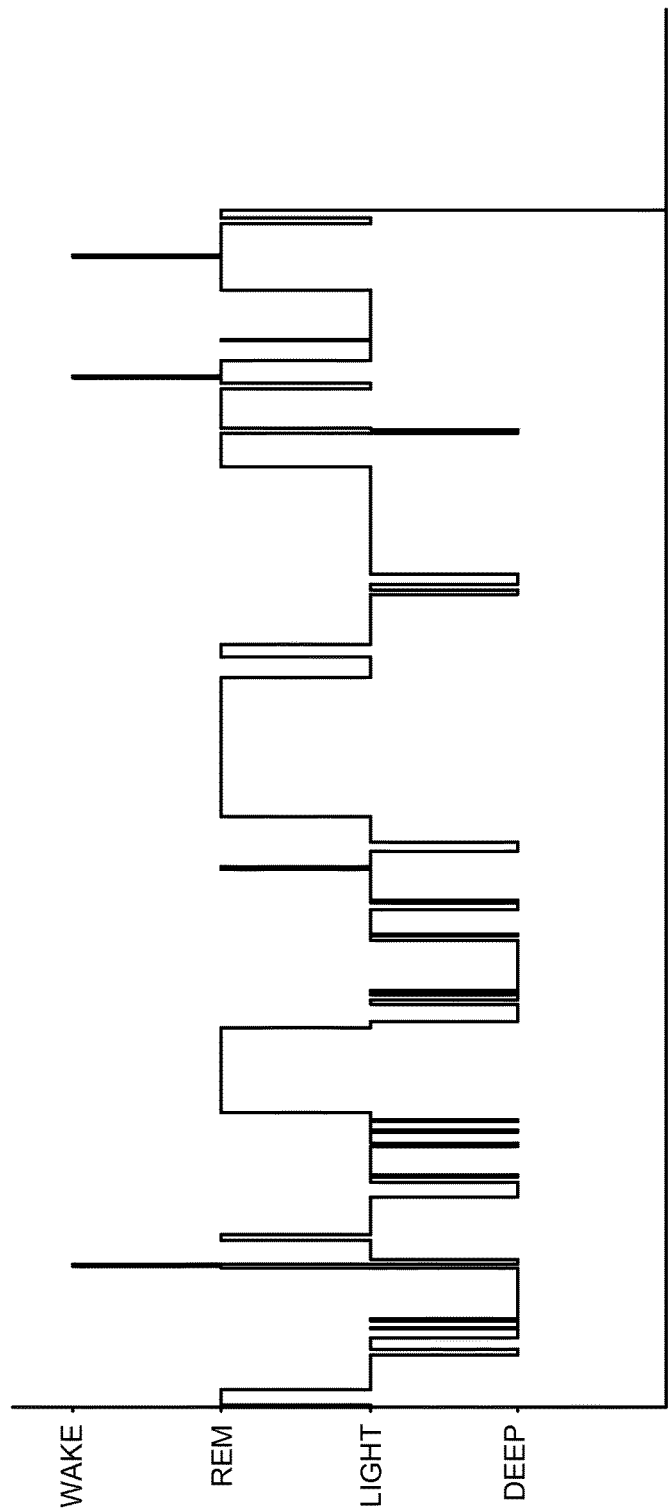

Turning briefly 4A-4C, each of FIGS. 4A, 4B, and 4C illustratively provides an example night's sleep information for a particular user, wherein sleep state is repeatedly characterized into one of 4 sleeping states (Wake, REM, Light, Deep) over successive time intervals, such as 30-second intervals. FIGS. 4A, 4B, and 4C correspond to 3 different individuals, respectively.

With reference to step 210 of FIG. 2, in some embodiments, information from at least 20 nights is received with hypnograms of sleep durations longer than three hours for all nights sampled, divided into epochs not larger than 1 minute in length. In some embodiments, the sleep information may be accumulated over several nights, such as for example 20 nights before providing sleep information to be received at step 210. In some embodiments, the nights include a minimum number of weekday nights and weekend nights, which will have different patterns for some individuals. In some embodiments, an iterative process of receiving sleep information may be applied wherein information acquired from each additional night is added to information acquired from previous nights, for a user or group of users. For example, in some embodiments, a rolling window of nights (such as 1 month, 3 months, or six months) may be used.

In some embodiments, acquired sleep information, which may be acquired from monitor 141 or user records, may require cleaning or filtering. For example, it has been shown that sometimes a user may dislodge the sensor component of monitor 141 from the user's head, may go to the bathroom and become out of range for sleep data acquisition, or may be awake for most of the night, thereby resulting in periods missing, erroneous, or otherwise unusable values over the night in which these incidents occur. In some embodiments, monitor 141 may simply characterize the user's sleeping state as unknown for these intervals. Therefore, in some embodiments, these periods of erroneous or missing information may be cleaned or filtered, for example, by imputing of filling in values, where only a small number of values are missing or erroneous, or by excluding the entire nights information where a larger number of values are missing or appear erroneous. Thus, in some embodiments, even where sleep information exists for 20 nights, some of these nights may be excluded. Additionally, while results may be determined based on a fewer number of nights, better results are likely to be produced where the number of nights is 24 nights or more.

In some embodiments, sleep information may come from more than one source, such as monitor 141 and user or patient health records, which may have been generated by past episodes of using monitor 141. For example in the case of a patient undergoing repeat testing using monitor 141, sleep information from past sensor-sessions wherein the user used monitor 141, may be used, in some embodiments.

Similarly, sleep information may include observational captures of data that may have been accumulated at other points of time. In some embodiments, software agents facilitate locating and identifying relevant additional data sources of sleep information, such as by identifying other records that match the user, and cleaning or preparing the data to be included.

At a step 220 the received information is assembled into timeseries. In some embodiments, the time series comprises one or more arrays (or row vectors) representing sleep information for an individual, wherein each array is associated with one night or sleeping period, and wherein an array includes one or more elements of values characterizing the individuals sleeping state over an interval of time. Thus for example, a 6 hour sleeping period wherein sleeping state is characterized every 30 seconds and wherein every 30-second period provides usable sleeping information, may be represented as an array of 720 elements, each element characterizing sleep for one 30-second interval over the 6 hours, in one embodiment.

In some embodiments, step 220 includes cleaning the time series information. The ordinal or hypnogram timeseries may be cleaned to remove any leading or trailing non-classified segments. For example leading and/or trailing zeros for epochs not classified or wherein the monitor 141 was sensing information but not while on the user's head.

At an step 230 nonlinear timeseries is determined. In some embodiments, step 230 is optional, and may provide more accurate results if included. Step 230 may comprise calculating second-order self-excited threshold autoregressive model (SETAR model) and/or neural network autoregressive model (NNET) based on the timeseries, in some embodiments. These models robustly capture non-linear and chaotic patterns in normal and abnormal sleepers.

In some embodiments, step 230 is facilitated by software services 126 of FIG. 1A using the tsDyn package in the R-System, or similar services for facilitating implementation of nonlinear autoregressive time series models. An example computer program routine for implementing tsDyn is shown in FIGS. 7A and 7B. The tsDyn operation casts an array of numbers into a dynamic series datatype (ts datatype) used by the R-System for handling timeseries. For example, each night of sleep information for an individual corresponds to an array of numbers such as a row vector comprising a one-dimensional array of 30-second time intervals wherein each element of the array has a value representing a 30-second characterization of sleeping state. The output is still a timeseries, but a longer time series.

In some instances whether to perform step 230 may be determined by the amount of data available. Step 240 may be used to impute values if there are gaps in an individuals timeseries record and to ascertain the quality of the raw timeseries values or identify segments wherein the raw values may be suspect. In certain circumstances, it may be desirable to have more available data (samples of sleep information) for more accurate determinations. For example, typical Lyupanov operations can require several thousand data points for accurate results. Therefore, in such circumstances an original, shorter timeseries may be simulated with an autoregressive model. The original timeseries essentially forms a seed from which a model (or models) is generated. For example, a timeseries comprising only 192 30-sec samples can be extended and simulated multiple times to generate a timeseries that may be 500 to 1000 samples in length. In embodiments, a SETAR or neural network model may be generated multiple times and then compared to determine whether the models substantially agree with the autoregressive coefficients by a lag number or R coefficients (correlation coefficients) in a neural network. Where multiple generations of the model appear to be stable, the model may be usable for extending the raw timeseries to a length that is likely to produce a more stable Lyapunov exponent.

If the data were sufficiently long enough, then step 230 may only be used for diagnostic purposes such as assessing the quality or stability of the results of the subsequent analysis, by determining whether the models are substantially different between individuals, for example. Suppose there are three individuals with sleep information received from forty nights, then for diagnostic purposes a comparison of the differences in the SETAR and/or NNET models for each individual and across all three individuals may be performed. Such diagnostic operations can be useful for software quality assurance (QA), for example by conducting release-to-release regression testing in a software QA environment.

Figure 5A:
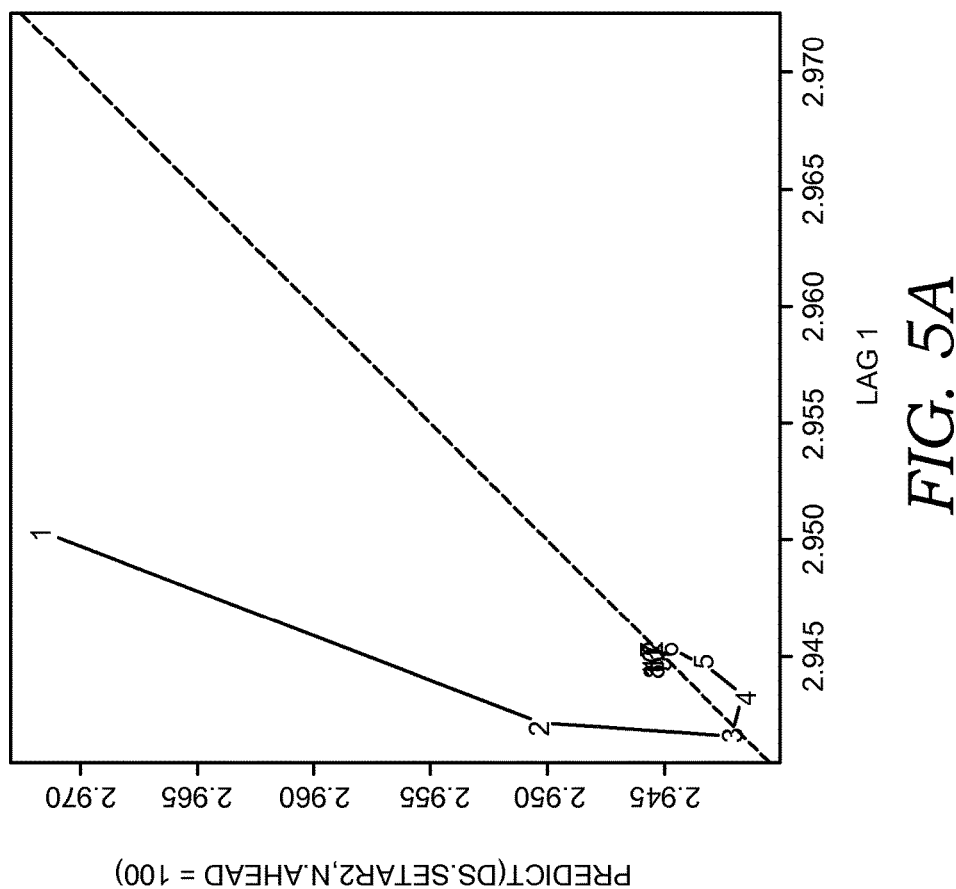
FIGS. 5A, 5B, and 5C each illustratively depict strange-attractor diagrams corresponding to coefficients of the nonlinear model for each sample-period over a night, for a particular user.
Figure 5B:
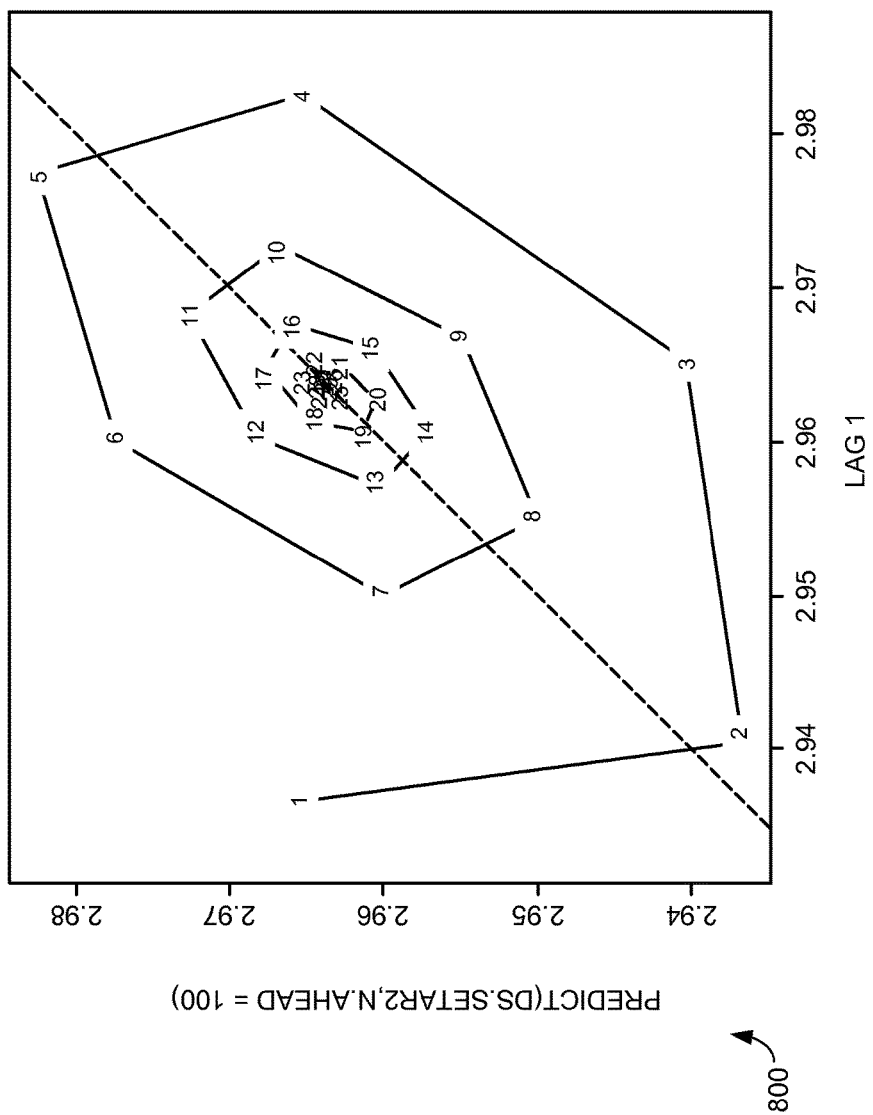
Figure 5C:
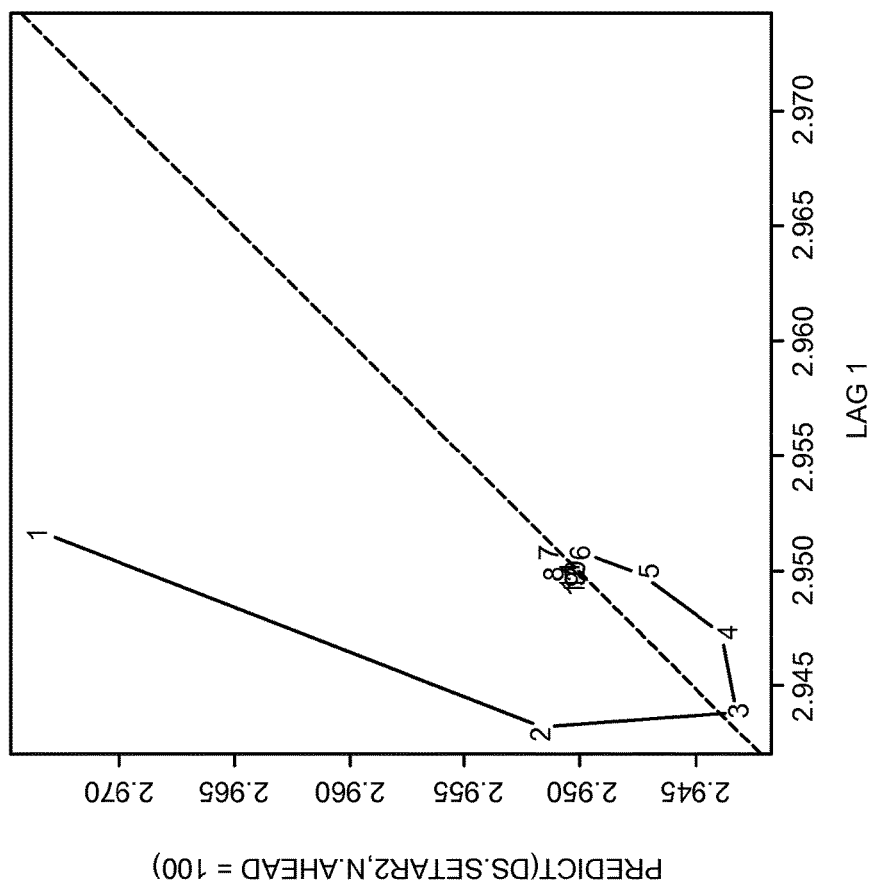

The tsDyn operation may also be used to generate a visual characterization of an individual's night sleep, sort of like a fingerprint for the night, for the individual. In particular, tsDyn facilitates identification of strange attractors (attractors with fractal structures) in sleep information for an individual, for example the self-excited autoregressive second order model lag 1 vs. the predicted value of that. Examples of such visual characterizations are depicted in FIGS. 5A-5C. Turning briefly to FIGS. 5A-5C, each of 5A, 5B, and 5C show a visual characterization of one night, for a different individual (three separate individuals, 5A, 5B, and 5C) wherein each number correspond to a sample within that given night. Such characterizations provide personalized medicine or personalized sleep-architectural imprint, and may also be used as a qualitative or visual way to see whether the SETAR or other NNET coefficients are different or the same as they were before, for this individual or population. Thus the characterizations may provide a subjective sense about how sleeping went on subjective nights. For example, FIG. 5B shows a pattern cycling towards a stable attractor.

Returning to FIG. 2, at a step 240, the largest Lyapunov exponent (LLE, $\lambda$) of the timeseries is determined. In some embodiments, step 240 calculates an LLE (a number) for each timeseries. For example, wherein a set of row vectors represents the nights of sleep information for an individual, each row vector comprising a one-dimensional array, the output of step 240 includes a column vector of LLEs, with one LLE determined for each night (each timeseries or row vector). In some embodiments, step 240 is facilitated by software services 126 of FIG. 1A using the tseriesChaos package in the R-System, or similar services for performing nonlinear time series operations. An example computer program routine for implementing tseriesChaos is shown in FIGS. 7A and 7B.

In some embodiments, the Kantz algorithm is used for determining the LLE for the timeseries of each night. In particular, the lyap_k( ) function, as shown in the example program routine of FIGS. 7A and 7B, is applied to the generated timeseries of step 230 or step 220, if step 230 is omitted. The lyap( ) function may then be applied to perform regression to estimate the LLE 2. The Kantz algorithm may produce a stable result for a smaller number of data points, such as one to two thousand data points, whereas other methods may require an order of data points greater (tens of thousands) to show a stable result.

Figure 8:
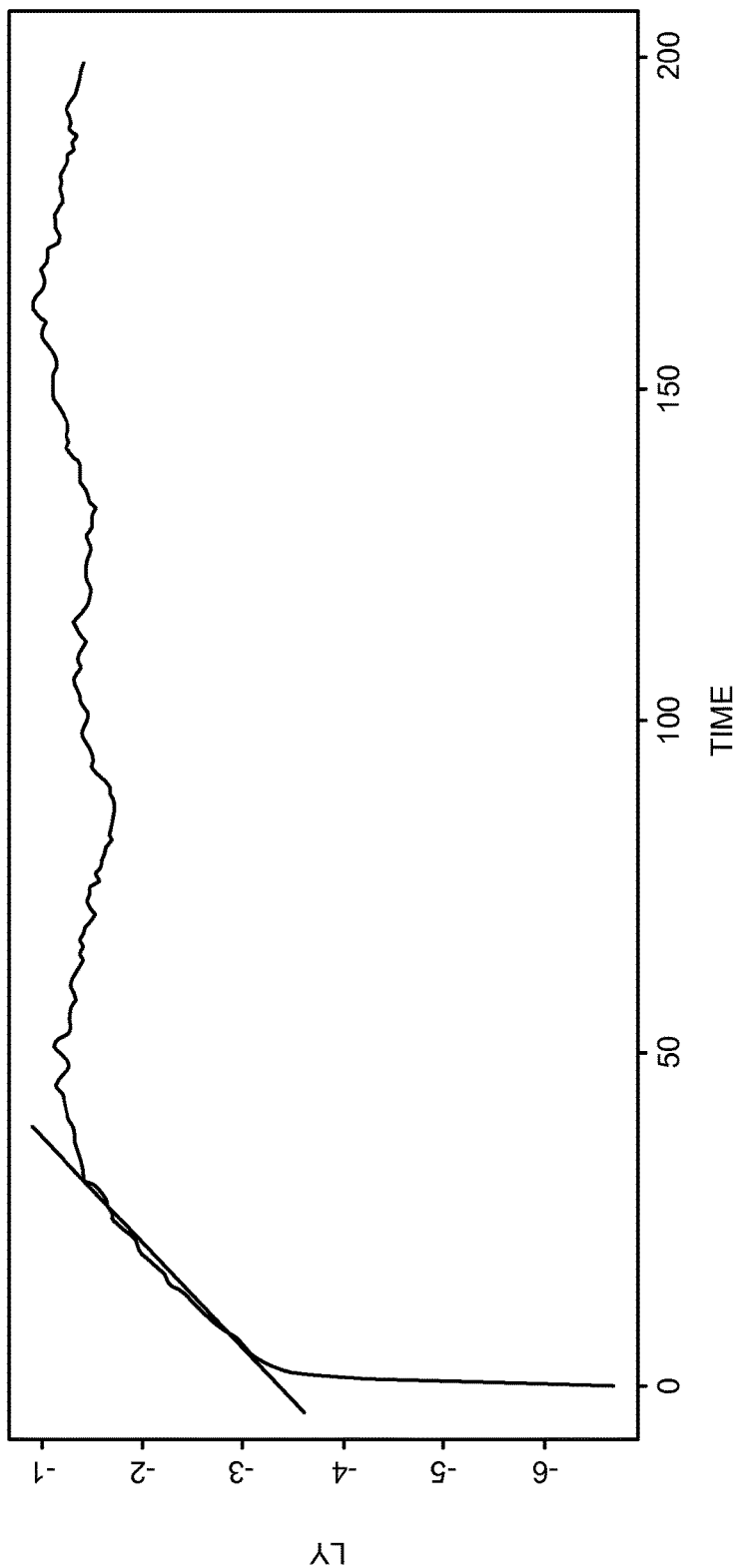
FIG. 8 illustratively depicts Lyapunov exponent information as a function of samples of time, with a tangent corresponding to the numerical measure of the LLE, representative of a typical night of sleep.

FIG. 8 shows an example graphical depiction of a largest Lyapunov exponent as determined by the Kantz algorithm.

FIG. 8 includes graph 800, which is representative of a typical night of sleep for an individual. (Graph 8, thus provides another example of personalized medicine.) As shown, the Lyupanov exponent is calculated across scales of time in samples (rather than seconds or minutes) for hundreds of samples and relates to the lag between consecutive time intervals. Thus it can be determined whether the Lyupanov exponent is scale-dependent for those scales of time. Near time zero and time close together indicate instability. In embodiments, tseriesChaos or similar routines may be applied essentially to identify intervals that show a reasonably linear regression. For example, a span of samples relatively collinear with a tangent, such as line 801. The numerical measure of LLE is given by the slope of line 801 in FIG. 8. Thus for each night a slope (representing the value of the LLE) is determined.

In some embodiments, determining LLE by the Kantz method may be facilitated by adding a level of random noise to the timeseries information. In particular, where the timeseries information comprises all integers then some methods for determining the LLE, such as Kantz, may not always converge or may otherwise fail by converging to a value that is not accurate. Accordingly, a solution to this problem is to introduce a small about of observational noise (small relative to the value of the data points in the timeseries). For example, a small Gaussian random number (or number based on another random function) may be added to each integer in the timeseries to re-fuzzify the values prior to determining the LLE. Therefore some embodiments of step 240 include adding a small amount of random noise to each timeseries before determining the LLE of each timeseries.

In some embodiments, step 240 further includes assembling the LLE values of the matched target and reference instances for facilitating statistical tests applied at a step 250. For example, for a given individual the output of step 240 might include a set of LLEs, one characterizing each night of sleep. In some embodiments, these LLEs are assembled to create a distribution that characterizes the individual and the architecture of their sleep across that time period. Unusual LLE values and patterns of values can serve as indicators of conditions affecting the individual or regression or progression of conditions, which might indicate the effectiveness of a treatment or side-effect from a treatment.

In some embodiments, a cumulative sum (cusum) operation or an iteration operation might be performed, for example by using a moving window over sequential LLE values (one LLE per night over a series of nights). Such operations may provide robust trend analysis to determine whether the pattern of the individual is being stable over time or is going one way or the other (higher or lower than what is normal for the individual). Such trend analysis may be used to determine whether the individual is progressing or regressing, for example whether an individual at risk for suicide is getting better or worse. An advantage provided by the cusum operation is that in some embodiments, it is autoranging and does not require input-adjustment or scaling. Additionally, the output of the cusum or other iteration operation can be used to generate a result that is provided to a caregiver, such as in the form of a visual display representing a patient's tending condition. For example, a neurologist who is examining the stroke recovery of a patient or a psychologist or social worker caring for a PTSD of a wounded warrior. Such a result may be useful for indicating that some new event has impacted a condition the patient, for example, triggered an exacerbation in the PTSD. Accordingly the caregiver may be informed to alter the treatment regimen, such as by adjusting the patient's meds, ordering additional cognitive therapy, or reaching out to the family of the patient.

At step 250, statistical measures for the determined LLE values and reference information are determined. For example statistical tests may be applied to determine whether an individual has departed from the population normal, which may be captured in a behavioral group. In some embodiments, wherein there are enough data for the individual, it may also be possible to determine a deviation from the normal for that patient, such as a trend over time indicating whether the patient is getting better or worse.

In some embodiments of step 250 comprises performing a t-test, Mann-Whitney test, other non-parametric tests, or suitable tests for comparing the values from the target subject to those of reference populations. In some embodiments, this may be used to confirm that the values determined from step 240 are sufficiently unlikely to be false-positives by comparing a p-value to a threshold, as described at a step 260, where p might be 0.05 using one of these tests. In particular, in some instances where data is not collected over a longer duration, the user data may be limited to sets of short series of several dozen data points. In such instances, the confidence that the assumptions for t-test or other tests assume a normal, symmetrical distribution cannot necessarily be determined.

In some embodiments a boundary for normal LLE for an individual is determined. For example, it is expected that the LLE value would probable increase slightly as an individual gets older. Thus the range for an LLE of an 80-year old would be different than that of a middle-aged person. Similarly, the range of an LLE for a man can be different than that for a woman. Additionally, some embodiments of the invention indicate that, given all the potential differences in LLE for age, gender, or other differences, with an n=3 confidence interval, LLE ranges tend to be slightly positive. More positive LLE values indicate a greater degree of chaos, such as changes between sleeping states for an individual. In some embodiments, the LLE reference range comprised 0.02 to 0.08. An LLE of exactly zero represents a perfectly stable attractor. A range value that is positive (such as 0.1 or greater) could indicate a problem that is diagnosable or treatable. For example, depression and psychosis, including treated and untreated/under-treated) can have LLE values outside a normal reference range (such as 0.02 to 0.08). The LLE can reveal abnormalities even when conventional sleep parameters, such as counting minutes of sleep, are within normal limits.

At step 260, a threshold comparison is performed to determine whether the target subject is statistically different than the reference population data, which may comprise data from a normal population or population having a specific condition, such as schizophrenia. In embodiments, the threshold value may be determined by statistical epidemiological criteria, for example representing a sensitivity that is necessary to detect a particular abnormality. Thus in some embodiments, the value of the threshold is derived based on the reference population. In some embodiments, the threshold may be empirically established as denoting statistically significant deviation from the range of LLE values for one or more reference groups.

In some embodiments the threshold value may be specified in one or more data tables, provided by a caregiver, identified by the labeling of a drug or provided by a pharmaceutical company, or determined by a software routine or software agent. In some embodiments, the threshold may be specific to the individual, may be by population (including sub-populations based on demographics or conditions) or by product, such as a drug, therapy, or other treatment. For example, as described previously, embodiments of the invention may be used to determine the effect of certain drugs on the condition of a patient, for better or worse. A given drug may have an associated threshold value or range indicating to caregivers that patients being treated by the drug may be expected to fall within this range or below the threshold.

At a step 270, where the threshold is not satisfied, then the target may be reported as not statistically different a reference group. On the other hand, if the threshold is satisfied, then at a step 280, the target subject may be reported as statistically different from the reference group. In some embodiments, matches (or differences) between a target and reference group may be provided to a clinician or caregiver, and may be reported as results displayed on interface 142 of FIG. 1A. In some embodiments, probable matches or differences determined in step 260 merit further considerations for intervention such as by implementing or modifying a treatment, or taking another action.

Turning back to FIGS. 7A and 7B, an example embodiment of computer program routines for implementing aspects of method 200 is provided in FIGS. 7A and 7B, which includes R-system packages for tsDyn, tseriesChaos, and further include generating nonlinear models, adding observational noise and applying lyap_k( ) and lyap functions, discussed above.

With reference now to FIGS. 3A-3C, output and results are provided for an example embodiment of the invention using sleep information including information such as shown for the three individuals of FIGS. 4A-4C, but acquired over a series of 30 to 40 nights. In this example embodiment, the non-linear timeseries SETAR and neural network models and Largest Lyapunov Exponent methods and subsystems were reduced to practice using a server cluster running the Linux operating system, the open-source statistical software package R, the R modules tseriesChaos and tsDyn, as described above. Retrieval of structured discrete items was performed using the Zeo™ EEG headset device. Each of FIGS. 3A, 3B, and 3C shows the LLE determined for each night, for the individual, and a ZQ number determined for the night (discussed above in connection to monitor 141).

With reference to FIGS. 6A and 6B, FIG. 6A provides additional statistical measures for an example night, and FIG. 6B shows the effect of various alternate distributions.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A non-transitory computer-readable media having computer-executable instructions embodied thereon that, when executed by a processor, cause a method of characterizing sleep architecture to be performed, the method comprising:
    acquiring a first set of sleep-related information for a target user via one or more sensors located in proximity to the target user;
    receiving a second set of sleep-related information associated with a reference population and including a range for largest Lyapunov exponent (LLE) values associated with the reference population;
    based on the first set of sleep-related information, determining a set of timeseries;
    based on the set of timeseries, determining an LLE value for each timeseries in the set of timeseries, thereby generating a set of LLE values;
    performing a comparison of the set of LLE values to a threshold to determine whether the target user is statistically different than the reference population based on the range for the LLE values associated with the reference population;
    based on the comparison determining that the target user is not statistically different than the reference population, designating the target user as associated with the reference population; and
    causing notification to be provided via an interface to a caregiver that the target user is associated with the reference population.

2. The computer-readable media of claim 1, wherein the threshold is determined based on the range for largest Lyapunov exponent (LLE) values associated with the reference population, and wherein the target user is determined as not statistically different where the set of LLE values is less than the threshold.

3. The computer-readable media of claim 1, wherein the reference population comprises a population of individuals of similar age and gender as the target user.

4. The computer-readable media of claim 1, wherein the reference population comprises a population of individuals having a condition affecting sleep.

5. A non-transitory computer-readable media having computer-executable instructions embodied thereon that, when executed by one or more computing devices, cause a method of characterizing sleep architecture to be performed, the method comprising:
    acquiring a first set of sleep-related information for a target user via one or more sensors located in proximity to the target user, wherein the one or more sensors sense one or more of electroencephalography signal activity or muscle activity;
    receiving a second set of sleep-related information associated with a reference population and including a range for largest Lyapunov exponent (LLE) values associated with the reference population;
    based on the first set of sleep-related information, determining a set of timeseries;
    based on the set of timeseries, determining an LLE value for each timeseries in the set of timeseries, thereby generating a set of LLE values;
    performing a threshold comparison to determine whether the set of LLE values is statistically different than the range for LLE values associated with the reference population;

based on the comparison determining a statistical departure of the set of LLE values from the range, designating the target user as not associated with the reference population; and causing notification to be provided via an interface to a caregiver that the target user is not associated with the reference population.

6. The computer-readable media of claim 5, wherein the reference population comprises a population of individuals of similar age and gender as the target user.

7. The computer-readable media of claim 5, further comprising determining whether a condition of the target user is progressing or regressing by performing a trend analysis on the set of LLE values.

8. The computer-readable media of claim 5, wherein determining an LLE value for each timeseries in the set of timeseries comprises using a Kantz algorithm.

9. The computer-readable media of claim 8, further comprising adding random noise to values of each timeseries, prior to determining the LLE value for each timeseries.

10. The computer-readable media of claim 5, further comprising:

based on the determined set of timeseries, generating a set of non-linear timeseries; and determining the LLE value for each non-linear timeseries in the set of non-linear timeseries.

11. The computer-readable media of claim 10, wherein the non-linear timeseries comprises one of a self-excited threshold autoregressive or neural network model.

12. A method of characterizing sleep architecture, the method comprising:

with one or more computing devices:

acquiring a first set of sleep-related information for a target user via one or more sensors located in proximity to the target user;

receiving a second set of sleep-related information associated with a reference population and including a range for largest Lyapunov exponent (LLE) values associated with the reference population;

based on the first set of sleep-related information, determining a set of timeseries;

based on the set of timeseries, determining an LLE value for each timeseries in the set of timeseries, thereby generating a set of LLE values;

performing a comparison of the set of LLE values to a threshold to determine whether the target user is statistically different than the reference population based on the range for the LLE values associated with the reference population;

based on the comparison determining that the target user is not statistically different than the reference population, designating the target user as associated with the reference population; and causing notification to be provided via an interface to a caregiver that the target user is associated with the reference population.

13. The method of claim 12, wherein the threshold is determined based on the range for largest Lyapunov exponent (LLE) values associated with the reference population, and wherein the target user is determined as not statistically different where the set of LLE values is less than the threshold.

14. The method of claim 12, wherein the reference population comprises a population of individuals of similar age and gender as the target user.

15. The method of claim 12, wherein the reference population comprises a population of individuals having a condition affecting sleep.

* * * * *

UNITED STATES PATENT AND TRADEMARK OFFICE
CERTIFICATE OF CORRECTION

PATENT NO. : 10,098,582 B1  
APPLICATION NO. : 14/279750  
DATED : October 16, 2018  
INVENTOR(S) : Douglas S. McNair et al.

Page 1 of 1

It is certified that error appears in the above-identified patent and that said Letters Patent is hereby corrected as shown below:

On the Title Page

Item (73) Assignee: Please remove "Cerner Innovations, Inc." and replace with --Cerner Innovation, Inc.--.

In the Drawings

Sheet 15 of 17 (FIG. 7A), Line 21: Please remove "occationally" and replace with --occasionally--.

In the Specification

Column 13, Line 57: Please remove "Lyupanov" and replace with --Lyapunov--.
Column 15, Line 4: Please remove "Lyupanov" and replace with --Lyapunov--.
Column 15, Line 8: Please remove "Lyupanov" and replace with --Lyapunov--.

Signed and Sealed this  
Eleventh Day of December, 2018

Andrei Iancu  
*Director of the United States Patent and Trademark Office*